United States Patent [19]
Brown

[11] Patent Number: 5,720,733
[45] Date of Patent: Feb. 24, 1998

[54] APPARATUS FOR DETERMINING AND RECORDING INJECTION DOSES IN SYRINGES USING ELECTRICAL CAPACITANCE MEASUREMENTS

[75] Inventor: Stephen J. Brown, Mountain View, Calif.

[73] Assignee: Raya Systems, Inc., Mountain View, Calif.

[21] Appl. No.: 681,314

[22] Filed: Jul. 22, 1996

Related U.S. Application Data

[63] Continuation-in-part of Ser. No. 278,929, Jul. 22, 1994, Pat. No. 5,569,212.

[51] Int. Cl.$^6$ .................................................. A61M 5/00
[52] U.S. Cl. ........................... 604/207; 604/246; 235/451; 222/23; 222/30
[58] Field of Search ................. 604/207–211, 246; 128/DIG. 1; 235/451; 222/23, 30

[56] References Cited

U.S. PATENT DOCUMENTS

| | | |
|---|---|---|
| 4,846,797 | 7/1989 | Howson et al. . |
| 4,853,521 | 8/1989 | Claeys et al. . |
| 4,950,246 | 8/1990 | Muller . |
| 4,978,335 | 12/1990 | Arthur, III . |
| 5,019,974 | 5/1991 | Beckers . |
| 5,176,502 | 1/1993 | Sanderson et al. . |
| 5,569,212 | 10/1996 | Brown . |
| 5,593,390 | 1/1997 | Castellano et al. . |
| 5,628,309 | 5/1997 | Brown . |
| 5,651,775 | 7/1997 | Walker et al. . |

*Primary Examiner*—Mark Bockelman
*Attorney, Agent, or Firm*—Lumen Intellectual Property Services

[57] ABSTRACT

An apparatus for electrically determining and recording the dose of an agent delivered with a syringe of the type having a barrel for holding the agent and a plunger for expelling the agent. The syringe includes a capacitive element having first and second conducting surfaces arranged such that the capacitance of the capacitive element varies in dependence upon the dose of agent contained in the barrel. An input terminal and an output terminal located on the outside of the syringe are electrically connected to the first and second conducting surfaces, respectively. The apparatus produces a voltage difference across the terminals, thereby charging the capacitive element. A capacitance meter measures the capacitance and a microprocessor calculates the dose from the measured capacitance. The calculated dose is recorded by a digital memory unit.

24 Claims, 5 Drawing Sheets

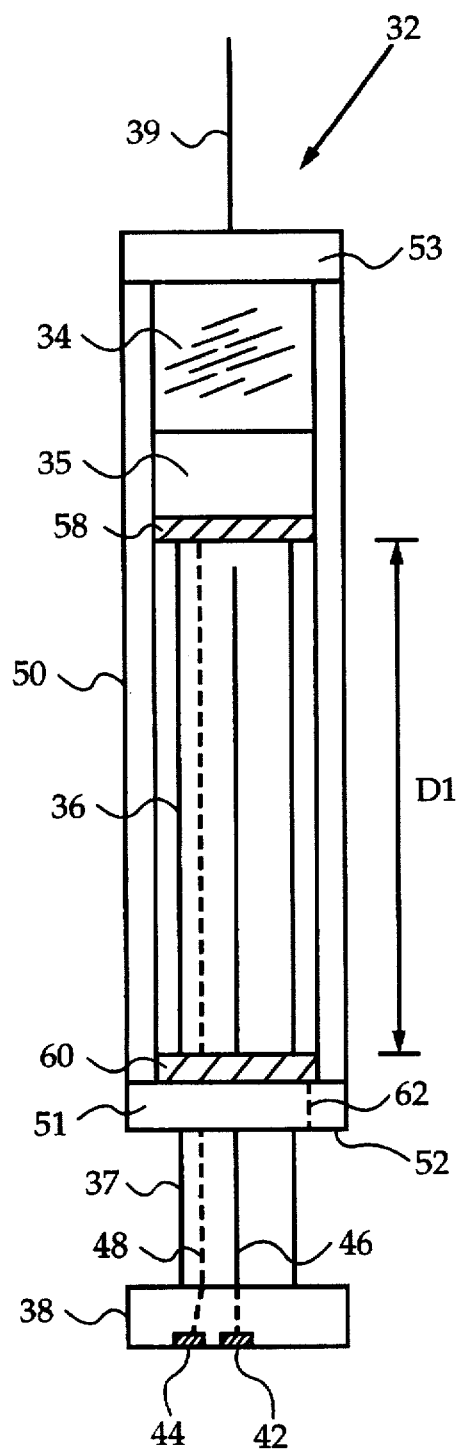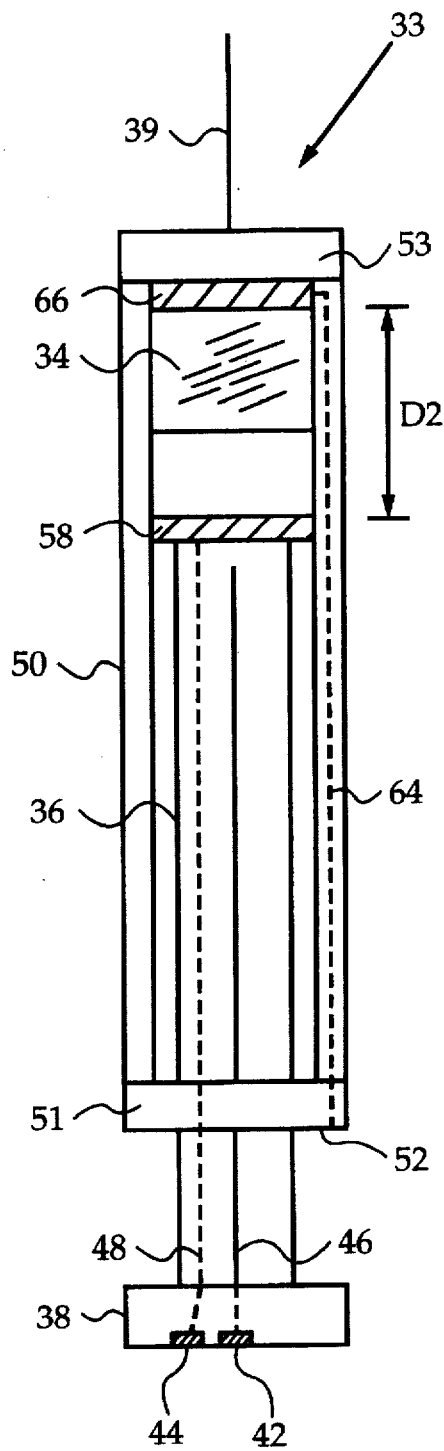
FIG. 2  FIG. 3

APPARATUS FOR DETERMINING AND RECORDING INJECTION DOSES IN SYRINGES USING ELECTRICAL CAPACITANCE MEASUREMENTS

CONTINUATION APPLICATION INFORMATION

This application is a continuation in part of application Ser. No. 08/278,929, filed Jul. 22, 1994 now U.S. Pat. No. 5,569,212. This application is also related to application Ser. No. 08/591,308 now U.S. Pat. No. 5,628,309, filed Jan.25, 1996. All of the above applications are hereby incorporated by reference.

BACKGROUND—FIELD OF THE INVENTION

The present invention relates to the field of injection syringes, and in particular to an apparatus for determining and recording the dose of an agent delivered with an injection syringe using electrical capacitance measurements.

BACKGROUND—DESCRIPTION OF PRIOR ART

In recent years, the value of keeping electronic medical records in place of paper records has been widely recognized in the healthcare industry. The use of electronic medical records allows healthcare providers and patients to store, retrieve, and share medical information with considerably more ease and accuracy. The sharing of medical information is particularly important in treatment programs involving self-administration of insulin, human growth hormone, or other medications in which patients themselves perform the injections and keep records.

Typically, these injections are performed using disposable syringes. Unfortunately, no adequate apparatus exists that electrically measures and records dose information from a disposable syringe. As a result, the patient performing the injection is burdened with the task of injecting the dose and then manually recording the dose amount in a log book.

Because of the frequency of such injections, often several times a day for diabetics, it becomes difficult to keep accurate records. Indeed, studies have shown that a patient's own records and recollections are often incomplete and inaccurate. Additionally, a patient may intentionally cheat while making self-recorded entries in an attempt to create a log book that will please his or her doctor. In the long-term this makes patient monitoring extremely difficult and jeopardizes the treatment program, possibly even endangering the patient's life.

Attempts have been made at developing electronic management systems for assisting patients in self-administered drug programs. For example, U.S. Pat. No. 5,019,974 issued to Beckers describes a hand-held, microprocessor-based recorder that interfaces with a master computer. The patient enters therapy information into the recorder via a keyboard. The recorder includes a display for displaying treatment therapy guidelines to the patient. The recorder also has a blood glucose meter for recording the patient's blood glucose levels.

Unfortunately, the recorder described by Beckers does not automatically measure and record dose information from a disposable syringe. After injecting a dose, the patient must manually enter the dose information into the recorder using switches or keys. Although this is an improvement over keeping written records on paper, the effectiveness of the drug program is still limited by the patient's recollections and recordings, which are unreliable.

Attempts have also been made at developing devices that deliver a predetermined dose of medication and record the dose amount. For example, U.S. Pat. No. 5,176,502 issued to Sanderson et al. on Jan 5, 1993 describes a syringe pump for expelling a preset dose of medication from a syringe. The syringe pump includes a syringe retainer for holding the syringe and a driver for engaging the plunger of the syringe. An electric motor pushes the driver and plunger into the syringe barrel to expel the medication.

The syringe pump further includes a monitoring circuit for monitoring the motion of the driver during the delivery of the medication. The monitoring circuit includes a linear potentiometer having an electrically conductive strip of resistive material. The resistive material is positioned such that it engages an electrical contact of the driver. The position of the electrical contact on the resistive strip varies the voltage of the monitoring circuit, thus indicating the position of the plunger inside the barrel. A microprocessor receives voltage signals from the monitoring circuit and compares the voltage signals to preprogrammed signals to determine if the plunger displacement corresponds to correct displacement for delivering the preset dose. A control mechanism connected to the microprocessor regulates the driver's movement to ensure the preset dose of medication is delivered.

Although the syringe pump described by Sanderson does allow electronic recording of dose information, it is only designed to deliver medication directly into an intravenous line. It is not designed to inject a patient directly nor can it measure and record a dose from a syringe unless the syringe pump pushes the plunger. Consequently, the syringe pump is of little use to an outpatient performing a self-injection treatment program.

Another device for injecting a preset dose of medication and for recording the injected dose is disclosed in U.S. Pat. No. 4,950,246 issued to Muller on Aug. 21, 1990. Muller describes a battery-operated injection pen having a pump rod driven by an electric motor. The electric motor is controlled by an electronic control unit that includes a microprocessor with a memory for storing dose information. The injection pen further includes a sensor connected to the control unit for electrically determining the position of the pump rod, and thus the amount of medication injected.

Although the injection pen described by Muller does electrically measure and record dose information, it has several disadvantages that preclude its widespread use. First, the injection pen is an expensive device requiring complicated electronic equipment to deliver and record doses. Second, because the injection pen integrates a syringe and electronic recorder into one device, it is not disposable. The patient must use it repeatedly for each injection, even after the injection pen has been contaminated with blood. Consequently, the injection pen does not provide an inexpensive, convenient, or hygienic solution to patients wishing to electrically measure and record injected dose information.

U.S. Pat. No. 4,853,521 issued to Ronald Claeys on Aug. 1, 1989 presents a programmable, intelligent reader unit which receives and records drug data using hand-held or fixed scanners. The scanners read bar codes in place on syringes, ampules, flow meters, etc. In addition, this intelligent reader allows the user to weigh a syringe before and after injection to determine and record the administered amount of medicine. Dosage data logged in this manner can be displayed or printed out in the form of a record.

While this apparatus comes closest to solving the problem, it involves many complicated steps of weighing syringes, scanning in bar codes, etc. These complex procedures as well as the high cost of the apparatus preclude effective home use. Additionally, the apparatus cannot be easily carried by the patient for recording doses while away from home. Thus, no inexpensive apparatus exists for electrically determining and recording dose information from a disposable syringe. Further, no such apparatus exists that is both simple in operation and easily carried by a patient.

OBJECTS AND ADVANTAGES OF THE INVENTION

In view of the above, it is an object of the present invention to provide an inexpensive apparatus for electrically determining and recording an injection dose delivered from a disposable syringe. It is another object of the invention to provide an apparatus that may be easily operated and carried by a user. A further object of the invention is to suit the apparatus to diabetic patients in particular.

These and other objects and advantages will become more apparent after consideration of the ensuing description and the accompanying drawings.

SUMMARY OF THE INVENTION

The invention presents an apparatus for determining and recording the dose of an agent delivered with a syringe. The syringe is of the type having a barrel for holding the agent and a plunger movably positioned in the barrel for expelling the agent. The syringe further includes a capacitive element having a first conducting surface coupled to the barrel and a second conducting surface coupled to the plunger for mutual movement therewith. The distance between the first conducting surface and the second conducting surface varies in dependence upon the position of the plunger inside the barrel. The position of the plunger inside the barrel determines the volume of agent contained in the barrel, so that the dose may be determined by a measure of the capacitance of the capacitive element.

In an alternative embodiment, the capacitive element includes a first conducting surface coupled to one side of the barrel and a second conducting surface coupled to the opposite side of the barrel. The agent functions as a dielectric between the conducting surfaces, so that the capacitance of the capacitive element varies in dependence upon the volume of the dose contained in the barrel. Consequently, the dose may be determined by a measure of the capacitance.

An input terminal located on the outside of the syringe is electrically connected to the first conducting surface. An output terminal located on the outside of the syringe is electrically connected to the second conducting surface. The apparatus includes a housing having a placement field for placement of the syringe during dose measurement. The field has an input contact for contacting the input terminal and an output contact for contacting the output terminal. A voltage generator is located within the housing to produce a voltage difference across the input contact and the output contact, thereby charging the capacitive element when the input contact is contacting the input terminal and the output contact is contacting the output terminal.

The apparatus further includes a capacitance meter connected to the input contact and output contact for measuring the capacitance of the capacitive element. A microprocessor is connected to the capacitance meter to calculate the dose from the measured capacitance. A recorder, such as a digital memory unit, records the calculated dose. The apparatus also includes an input/output port connected to the recorder so that recorded data may be transmitted through the input/output port to a host computer.

BRIEF DESCRIPTION OF THE DRAWINGS

FIG. 2 is a schematic side view of a syringe according to the invention.

FIG. 3 is a schematic side view of another syringe according to the invention.

DESCRIPTION

Figure 1:
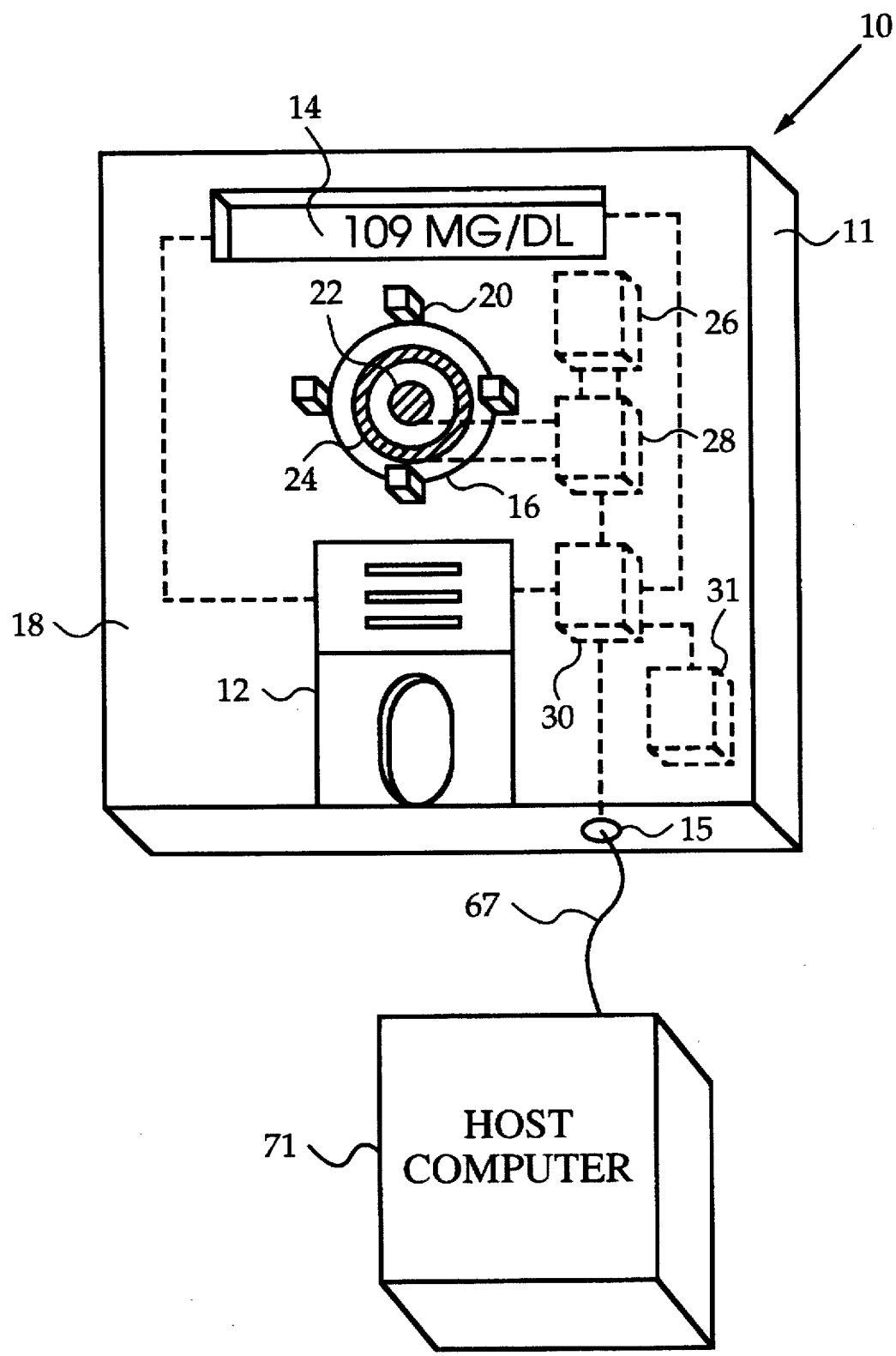
FIG. 1 is a three dimensional, schematic view of an apparatus according to the invention.
Figure 4:
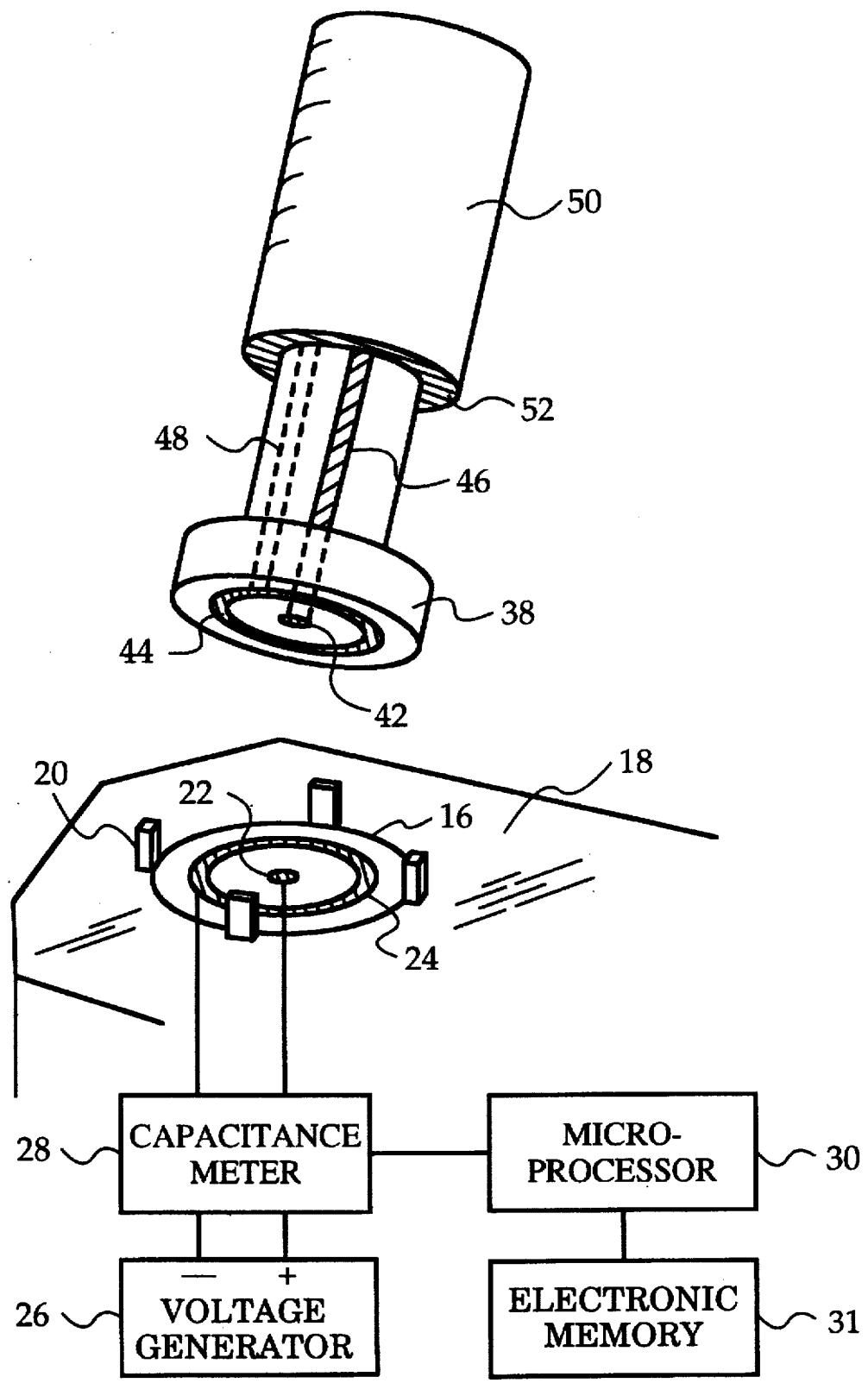
FIG. 4 is a perspective view and a partial block diagram of the syringe of FIG. 2 being placed on the apparatus of FIG. 1 for dose measurement.

A preferred embodiment of the invention is illustrated in FIGS. 1, 2, and 4. Referring to FIG. 2, a syringe 32 has a barrel 50 for holding an agent 34. Barrel 50 has an insertion end 51 and an injection end 53. A plunger 36 having a piston section 35, a plunger rod 37, and a cap 38 is inserted through insertion end 51. A needle 39 is attached to injection end 53 such that needle 39 is in fluid communication with barrel 50. Plunger 36 is movably positioned in barrel 50 for expelling a dose of agent 34 through needle 39. Agent 34 occupies the inner volume of barrel 50 between piston section 35 and injection end 53.

A conducting ring 60 is fixably attached to the inner surface of barrel 50 at insertion end 51. Ring 60 is of sufficient dimensions to allow plunger 36 to freely slide through ring 60. A conducting ring 58 is mounted to plunger 36 adjacent piston section 35. Ring 58 is fixably mounted to plunger 36 for mutual movement with plunger 36 inside barrel 50. Rings 58 and 60 are made of an electrically conductive material, preferably copper, and have sufficient surface areas to function as a capacitive element within syringe 32. Rings 58 and 60 are separated by a distance D1 that varies in dependence upon the position of plunger 36 inside barrel 50.

Cap 38 has an input terminal 42 and an output terminal 44. Terminals 42 and 44 are made of an electrically conductive material, preferably copper. One end of a conducting strip 46 is attached to terminal 42. Conducting strip 46 extends from terminal 42 through cap 38 and along the outside surface of rod 37 parallel to the longitudinal axis of rod 37. Strip 46 terminates in a second end on the surface of rod 37 before reaching ring 58, ensuring that strip 46 does not electrically connect ring 58 to terminal 42.

Barrel 50 has a rim 52 at insertion end 51. Rim 52 is lined with an electrically conductive material, preferably copper. Some of the electrically conductive material wraps inside barrel 50 to ensure rim 52 is in electrical contact with strip 46. A junction line 62 electrically connects rim 52 to conducting ring 60 such that ring 60 is electrically connected to terminal 42 through line 62, rim 52, and strip 46. A conducting strip 48 electrically connects output terminal 44 to conducting ring 58. Strip 48 extends from terminal 44 to ring 58 without contacting rim 52. In the preferred embodiment, this is accomplished by molding strip 48 into the surface of plunger 36. In an alternative embodiment, plunger 36 is hollow and strip 48 is routed along an inner surface of plunger 36.

Referring to FIG. 1, an apparatus 10 has a housing 11 for holding the components of apparatus 10. Housing 11 is sufficiently compact to allow apparatus 10 to be hand-held and carried by a user. The top surface of housing 11 has a face plate 18. A circular placement field 16 is delineated on face plate 18. Placement field 16 is bordered on four sides by rigid positioning studs 20. Placement field 16 includes a circular input contact 22 positioned at the center of field 16 and a ring-shaped output contact 24 positioned concentrically to input contact 22. Both input contact 22 and output contact 24 are made of an electrically conductive material, preferably copper.

Below face plate 18, contacts 22 and 24 are connected to a capacitance meter 28. Meter 28 is for measuring a capacitance C of rings 58 and 60, as will be explained in the operation section below. In the preferred embodiment, meter 28 is of the type that produces a digital measurement of capacitance C. In an alternative embodiment, meter 28 is of the type that produces an analog measurement of capacitance C. In this alternative embodiment, meter 28 is connected to an analog to digital converter (not shown) that converts the analog measurement into a digital measurement. A voltage generator 26 is connected to contacts 22 and 24 through capacitance meter 28 such that voltage generator 26 applies a constant voltage difference V across input contact 22 and output contact 24 through meter 28.

A microprocessor 30 is connected to meter 28 such that microprocessor 30 receives the digital measurement of capacitance C from meter 28. Microprocessor 30 is programmed to calculate the dose of agent 34 in barrel 50 from the measurement of capacitance C, as will be explained in the operation section below. An electronic memory 31 is connected to microprocessor 30 such that memory 31 records the dose calculated by microprocessor 30. In the preferred embodiment, memory 31 is a digital memory unit.

Apparatus 10 further includes a testing device 12. Device 12 is of the type that tests a physical condition of a user and produces a digital value representative of the physical condition. Device 12 is connected to memory 31 such that memory 31 records the digital value representative of the physical condition. In the preferred embodiment, device 12 is a blood glucose meter and the digital value represents the user's blood glucose level.

A display 14 is recessed in face plate 18 and connected to memory 31 through microprocessor 30. Display 14 is for displaying to the user recorded data stored in memory 31. An input/output port 15 is located on the outer surface of housing 11. Port 15 is connected to memory 31 through microprocessor 30 such that recorded data in memory 31 may be transmitted through port 15 to a host computer 71 through a data connection cord 67.

FIG. 4 illustrates in detail the positioning of cap 38 on field 16 for dose measurement. Field 16 is designed for receiving cap 38 such that input terminal 42 contacts input contact 22 and output terminal 44 contacts output contact 24. Input terminal 42 is circular and positioned at the center of the outer surface of cap 38. Output terminal 44 is ring-shaped and positioned concentrically to input terminal 42 on the outer surface of cap 38. Terminal 42 has the same shape and dimensions as contact 22 and terminal 44 has the same shape and dimensions as contact 24. Positioning studs 20 are located around field 16 for aligning cap 38 on field 16. Studs 20 are positioned such that when cap 38 is placed on field 16 within positioning studs 20, terminals 42 and 44 establish electrical contact with contacts 22 and 24, respectively.

The operation of the preferred embodiment is illustrated in FIGS. 1, 2, and 4. To determine a blood glucose level, the user places a finger on device 12. Device 12 draws blood from the user's finger, tests the blood, and produces the digital value representative of the user's blood glucose level. This value is recorded in memory 31 and displayed on display 14 as a "blood glucose level" measurement. The user can now use this measurement to determine an appropriate dose of agent 34 to inject.

Before injecting the dose, the user first presses the outer surface of cap 38 against field 16. When cap 38 is properly pressed between positioning studs 20, input contact 22 and output contact 24 establish electrical contact with input terminal 42 and output terminal 44, respectively. Meanwhile, voltage generator 26 applies voltage difference V across input contact 22 and output contact 24.

Voltage difference V causes an electric current I to flow to ring 58 and ring 60 and remain there in the form of accumulated charge, thereby charging the capacitive element. This condition is governed by the capacitance equation V=Q/C, where C is the capacitance of the system including ring 58 and ring 60. In turn, capacitance C is determined by the equation $C=Ae_r e_o/D_1$ where A is the surface area on which the charge accumulates, $e_r$ is the relative permittivity of the dielectric material between the plates, $e_o$ is a constant, and $D_1$ is the distance between ring 60 and ring 58.

The surface area A of ring 60 and ring 58 remain constant, as does the relative permittivity $e_r$ of rod 37. Thus, capacitance C is just inversely proportional to distance $D_1$. Meanwhile, distance $D_1$ defines the position of plunger 36 in barrel 50. Because agent 34 occupies the inner volume of barrel 50 between piston 35 and injection end 53, the length of plunger 36 inside barrel 50 defines the dose of agent 34 in barrel 50. Thus, a measurement of capacitance C indicates the dose of agent 34 in barrel 50.

The measurement of capacitance C is performed by meter 28 and received by microprocessor 30. Microprocessor 30 calculates the dose of agent 34 from the measurement of capacitance C and records the dose in memory 31. Display 14 also displays the calculated dose as a "dose selected" measurement. This alerts the user that the injection of agent 34 can now be performed. After recording a desired number of doses, the user transmits the dose records recorded in memory 31 through port 15 to host computer 71.

In the preferred embodiment, microprocessor 30 is programmed during the manufacture of apparatus 10 with a table of values for performing the dosage calculation. The table includes a range of possible values of capacitance C, and a corresponding dose volume for each value of capacitance C. Upon receiving a capacitance measurement, microprocessor 30 retrieves the dose volume corresponding to the capacitance measurement from the table. The table of values is created by measuring capacitance C with meter 28 for various known volumes of agent 34 in barrel 50. The measured capacitance for each known volume is then placed in the table. To create a precise table, at least ten known volumes of agent 34 ranging from a full barrel to an empty barrel should be measured to determine the corresponding capacitance of ring 58 and ring 60.

Of course, many other methods of calculating dose information from measurements of capacitance C are possible. For example, in one alternative embodiment, microprocessor 30 is programmed to calculate doses using a mathematical function derived from the table of values described in the preferred embodiment. Using the known volumes of agent 34 and the corresponding capacitance measurements produced by meter 28, a graph of dose volume as a function of measured capacitance is created. By interpolating from the known points on the graph, a mathematical function is derived describing the relationship of measured capacitance to dose volume. Microprocessor 30 then uses the derived mathematical function to calculate dose volumes from the measured capacitance. Specific techniques for calibrating an electronic apparatus by interpolating from test measurements are well known in the art.

The advantage of the apparatus described in the preferred embodiment is that it electrically measures doses directly from an injection syringe and digitally records the dose measurements. The user is not burdened with manually entering the dose information into a log. Additionally, the dose information recorded is more accurate than a user's manual records, which have been shown to be unreliable. Because the syringe requires no electronic equipment, it is manufactured very inexpensively and may be disposed of by the user following its use.

A second embodiment of the invention is shown in FIG. 3. The second embodiment differs from the preferred embodiment in that conducting ring 60 has replaced by a conducting plate 66. Conducting plate 66 is fixably attached to the inner surface of barrel 50 at injection end 53. Plate 66 has a hole (not shown) in its center allowing fluid communication between needle 39 and barrel 50.

Plate 66 is made of an electrically conductive material, preferably copper, and has a sufficient surface area to function as a capacitive element in conjunction with ring 58. Ring 58 and plate 66 are separated by a distance D2 that varies in dependence upon the position of plunger 36 inside barrel 50. A conducting line 64 electrically connects plate 66 to rim 52 such that plate 66 is electrically connected to input terminal 42 through line 64, rim 52, and strip 46. Line 64 is molded into the side surface of barrel 50 to ensure that line 62 does not contact ring 58.

The operation of the second embodiment is similar to the operation of the preferred embodiment. The primary difference is that meter 28 measures a capacitance C of ring 58 and plate 66 rather than the capacitance of rings 58 and 60. Apparatus 10 is calibrated to calculate doses from capacitance measurements of ring 58 and plate 66 in the same manner as described in the preferred embodiment. Other than the differences described, the operation and advantages of this second embodiment are the same as those described in the preferred embodiment above.

Figure 5:
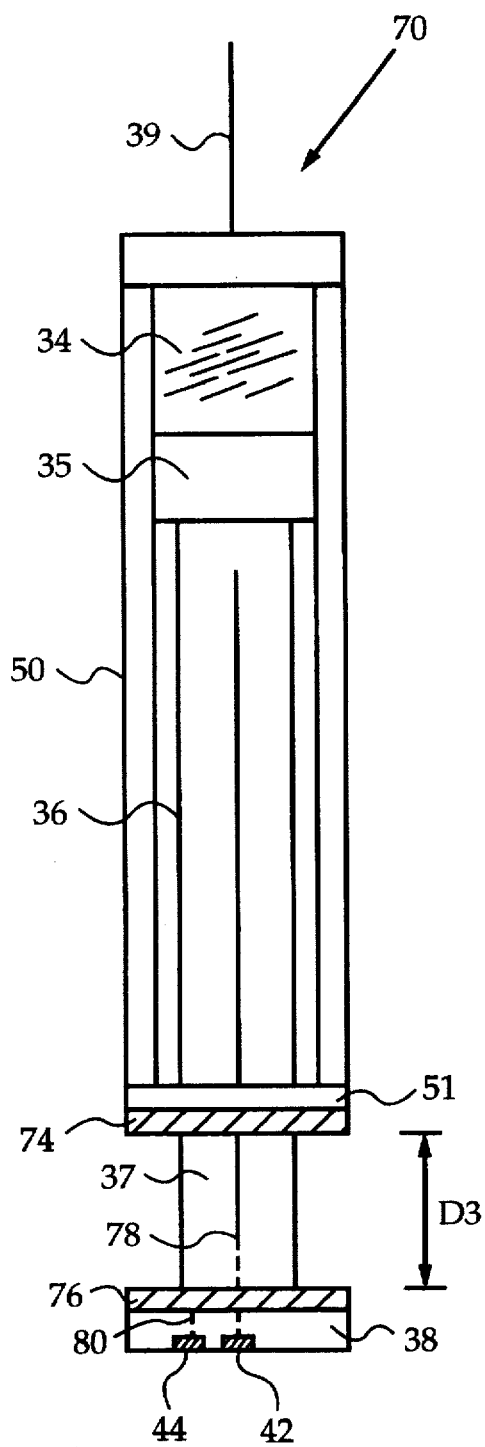
FIG. 5 is a schematic side view of another syringe according to the invention.

A third embodiment of the invention is shown in FIG. 5. The third embodiment differs from the preferred embodiment in that the capacitive element includes a first conducting ring 74 and a second conducting ring 76. Conducting ring 74 is fixably attached to the outer surface of barrel 50 at insertion end 51 such that ring 74 contacts the outer surface of rod 37. Conducting ring 76 is coupled to the inner surface of cap 38. Rings 74 and 76 are made of an electrically conductive material, preferably copper, and have sufficient surface areas to function as a capacitive element.

Rings 74 and 76 are separated by a distance D3 that varies in dependence upon the position of plunger 36 inside barrel 50. A conducting line 80 electrically connects terminal 44 to ring 76 through cap 38. One end of a conducting line 78 is connected to terminal 42. Line 78 is routed through cap 38 and a hole (not shown) through the center of ring 76 such that line 78 does not electrically contact ring 76. A short portion of line 78, typically 5 to 10 mm, is molded into rod 37 as indicated by the dotted line in FIG. 5. Line 78 then emerges on the outer surface of rod 37 and extends to ring 74 such that ring 74 is electrically connected to terminal 42 through line 78.

The operation of the third embodiment is similar to the operation of the preferred embodiment. The primary difference is that meter 28 measures a capacitance C of rings 74 and 76 rather than the capacitance of rings 58 and 60. Apparatus 10 is calibrated to calculate doses from capacitance measurements of rings 74 and 76 in the same manner as described in the preferred embodiment. Other than the differences described, the operation and advantages of this second embodiment are the same as those described in the preferred embodiment above.

Figure 6:
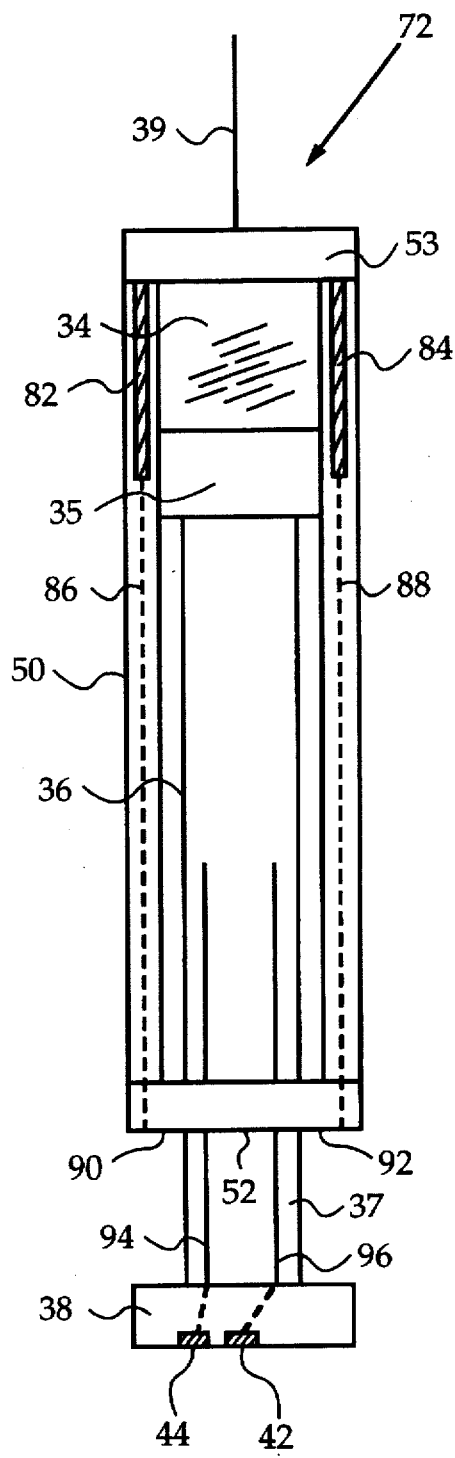
FIG. 6 is a schematic side view of another syringe according to the invention.
Figure 7:
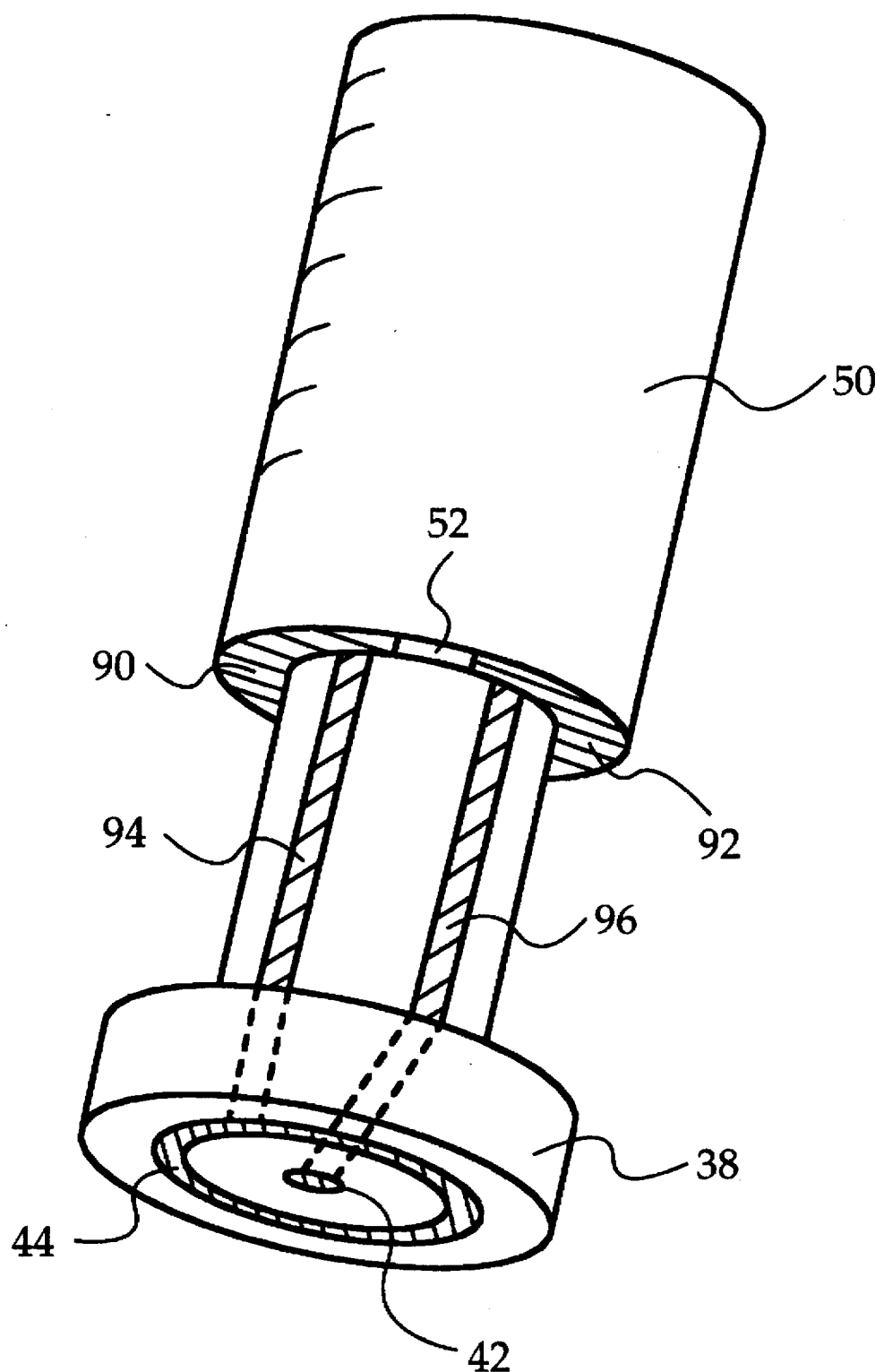
FIG. 7 is a perspective view of the syringe of FIG. 6 being placed on the apparatus of FIG. 1 for dose measurement.

A fourth embodiment of the invention is shown in FIGS. 6–7. A syringe 72 has a first conducting plate 82 coupled to one side of barrel 50 at injection end 53. A second conducting plate 84 is coupled to the opposite side of barrel 50 at injection end 53. Plates 82 and 84 are preferably molded into barrel 50 such that plates 82 and 84 do not directly contact agent 34. Plates 82 and 84 are made of an electrically conductive material, preferably copper, and have sufficient surface areas to function as a capacitive element. One end of a conducting line 86 is connected to plate 82. Line 86 is molded into the surface of barrel 50 and extends to rim 52. Similarly, one end of a conducting line 88 is connected to plate 84. Line 88 is molded into the surface of barrel 50 and extends to rim 52.

FIG. 7 illustrates rim 52 in greater detail. Rim 52 includes a first conducting section 90 and a second conducting section 92. Sections 90 and 92 are lined with an electrically conductive material, preferably copper. Sections 90 and 92 are separated by a non-conductive section of rim 52 such that sections 90 and 92 are not in electrical contact. Some of the electrically conductive material of section 90 wraps inside barrel 50 to ensure section 90 is in electrical contact with a conducting strip 94. Similarly, some of the electrically conductive material of section 92 wraps inside barrel 50 to ensure section 92 is in electrical contact with a conducting strip 96.

Referring again to FIG. 6, one end of strip 94 is connected to terminal 44. Strip 94 is routed through cap 38 and along the outer surface of rod 37 to section 90 such that plate 82 is electrically connected to terminal 44 through line section 90, and strip 94. One end of strip 96 is connected to terminal 42. Strip 96 is routed through cap 38 and along the outer surface of rod 37 to section 92 such that plate 84 is electrically connected to terminal 42 through line 88, section 92, and strip 96.

The operation of the fourth embodiment is similar to the operation of the preferred embodiment described above. Before injecting the dose, the user first presses the outer surface of cap 38 against field 16 and voltage generator 26 applies voltage difference V across input contact 22 and output contact 24. Voltage difference V causes electric current I to flow to plates 82 and 84 and remain there in the form of accumulated charge, thereby charging the capacitive element.

The primary difference between the operation of the fourth embodiment and the preferred embodiment is that capacitance C of plates 82 and 84 varies in dependence upon the relative permittivity $e_r$ of the dielectric material separating plates 82 and 84 rather than the distance separating plates 82 and 84. Referring again to the capacitance equation $C = A e_r e_o / D$, distance D separating plates 82 and 84, surface area A, and permittivity of empty space $e_o$ remain constant throughout the use of syringe 72. However, relative permittivity $e_r$ varies in dependence upon the volume of agent 34 contained in barrel 50.

Referring to FIG. 6, the dielectric material separating plates 82 and 84 consists of agent 34 and plunger 36. As the volume of agent 34 in barrel 50 increases, a larger portion of the dielectric material consists of agent 34 and a smaller portion of the dielectric material consists of plunger 36. Conversely, as the volume of agent 34 in barrel 50 decreases, a larger portion of the dielectric material consists of plunger 36 and a smaller portion of the dielectric material consists of agent 34. Because agent 34 and plunger 36 have different relative permittivities, the relative permittivity $e_r$ between plates 82 and 84 varies with the dose of agent 34 contained in barrel 50. Thus a measurement of capacitance C of plates 82 and 84 indicates the dose of agent 34 contained in barrel 50.

The measurement of capacitance C is performed by meter 28 and received by microprocessor 30. Microprocessor 30 calculates the dose of agent 34 from the measurement of capacitance C and records the dose in memory 31. Microprocessor 30 is calibrated to calculate doses from capacitance measurements of plates 82 and 84 in the same manner as described in the preferred embodiment. Other than the differences described, the operation and advantages of this second embodiment are the same as those described in the preferred embodiment above.

SUMMARY, RAMIFICATIONS, AND SCOPE

Although the above description includes many specificities, these should not be construed as limitations on the scope of the invention, but merely as illustrations of some of the presently preferred embodiments. Many other embodiments of the invention are possible. For example, in one alternative embodiment, the microprocessor is eliminated from the apparatus so that the capacitance measurements are recorded directly into the electronic memory. In this embodiment, the host computer is programmed to calculate the doses from the received capacitance measurements in the same manner as the microprocessor of the preferred embodiment.

Additionally, the placement field may have shapes differing from the circular shape described. The placement field could be square, hexagonal, or any other shape that aids a user in placing a syringe on the apparatus. Additionally, the placement field could be recessed in the face plate so that the positioning studs are unnecessary. In a particularly advantageous embodiment, the housing includes a syringe holder for conveniently storing the syringe with the apparatus.

Furthermore, the apparatus is not limited to measuring and recording doses from only one size syringe. In another embodiment, the apparatus includes a microprocessor which is programmed to calculate doses from syringes of different sizes. The microprocessor is connected to a user interface through which the user enters the size of the syringe he or she is using. Moreover, the apparatus is not limited to aiding a self-care diabetes program. It may be used to aid in the administration of any treatment plan that requires injections.

Therefore, the scope of the invention should be determined not by the examples given but by the appended claims and their legal equivalents.

I claim:

1. In combination with a syringe, an apparatus for determining and recording a dose of an agent delivered with said syringe, said syringe being of the type comprising:
    a) a barrel for holding said agent;
    b) a plunger movably positioned in said barrel for expelling said agent;
    c) a capacitive element comprising a first conducting surface coupled to said barrel and a second conducting surface coupled to said plunger for mutual movement therewith such that the distance between said first conducting surface and said second conducting surface varies in dependence upon the position of said plunger inside said barrel;
    d) an input terminal located on the outside of said syringe and electrically connected to said first conducting surface;
    e) an output terminal located on the outside of said syringe and electrically connected to said second conducting surface;

said apparatus comprising:
    a) a housing;
    b) a field on the outside of said housing, said field having an input contact for contacting said input terminal and an output contact for contacting said output terminal;
    c) a voltage generating means for producing a voltage difference across said input contact and said output contact, thereby charging said capacitive element when said input contact is contacting said input terminal and said output contact is contacting said output terminal;
    d) a measuring means connected to said input contact and said output contact for measuring the capacitance of said capacitive element and for calculating from the capacitance said dose; and
    e) a recording means connected to said measuring means for recording said dose.

2. The combination syringe and apparatus of claim 1, further comprising an input/output port located on a surface of said housing and connected to said recording means for transmitting recorded data from said recording means to a host computer.

3. The combination syringe and apparatus of claim 1, further comprising a testing means for testing a physical condition of a user and for producing a value representative of said physical condition, said testing means being connected to said recording means such that said recording means records said value.

4. The combination syringe and apparatus of claim 3, wherein said testing means comprises a blood glucose meter and said value represents a blood glucose level.

5. The combination syringe and apparatus of claim 1, further comprising a display recessed in said housing and connected to said recording means for displaying recorded data.

6. The combination syringe and apparatus of claim 1, wherein said input terminal and said output terminal are located on a cap of said plunger.

7. The combination syringe and apparatus of claim 6, wherein said input terminal is circular and positioned at the center of said cap and wherein said output terminal is ring-shaped and positioned concentrically to said input terminal.

8. The combination syringe and apparatus of claim 6, wherein said input contact is circular and positioned at the center of said field and wherein said output contact is ring-shaped and positioned concentrically to said input contact.

9. The combination syringe and apparatus of claim 6, wherein said field is bordered by a positioning means for aligning said cap on said field such that when said cap is placed within said positioning means, said input terminal contacts said input contact and said output terminal contacts said output contact.

10. The combination syringe and apparatus of claim 1, wherein said first conducting surface comprises a first conducting ring attached to an inner surface of said barrel at the end of said barrel through which said plunger is inserted and wherein said second conducting surface comprises a second conducting ring mounted to said plunger adjacent a piston section of said plunger.

11. The combination syringe and apparatus of claim 1, wherein said first conducting surface comprises a conducting plate attached to an inner surface of said barrel at the end of said barrel through which said agent is expelled and wherein said second conducting surface comprises a conducting ring mounted to said plunger adjacent a piston section of said plunger.

12. The combination syringe and apparatus of claim 1, wherein said first conducting surface comprises a first conducting ring attached to an outer surface of said barrel at the end of said barrel through which said plunger is inserted and wherein said second conducting surface comprises a second conducting ring coupled to a cap of said plunger.

13. The combination syringe and apparatus of claim 1, wherein said recording means comprise a digital memory unit.

14. The combination syringe and apparatus of claim 1, wherein said housing is sufficiently compact to enable said apparatus to be hand-held and carried by a user.

15. In combination with a syringe, an apparatus for determining and recording a dose of an agent delivered with said syringe, said syringe being of the type comprising:

a) a barrel for holding said agent;

b) a plunger movably positioned in said barrel for expelling said agent;

c) a capacitive element comprising a first conducting surface coupled to one side of said barrel and a second conducting surface coupled to the opposite side of said barrel such that the capacitance of said capacitive element varies in dependence upon the volume of said dose contained in said barrel;

d) an input terminal located on the outside of said syringe and electrically connected to said first conducting surface;

e) an output terminal located on the outside of said syringe and electrically connected to said second conducting surface;

said apparatus comprising:

a) a housing;

b) a field on the outside of said housing, said field having an input contact for contacting said input terminal and an output contact for contacting said output terminal;

c) a voltage generating means for producing a voltage difference across said input contact and said output contact, thereby charging said capacitive element when said input contact is contacting said input terminal and said output contact is contacting said output terminal;

d) a measuring means connected to said input contact and said output contact for measuring the capacitance of said capacitive element and for calculating from the capacitance said dose; and e) a recording means connected to said measuring means for recording said dose.

16. The combination syringe and apparatus of claim 15, further comprising an input/output port located on a surface of said housing and connected to said recording means for transmitting recorded data from said recording means to a host computer.

17. The combination syringe and apparatus of claim 15, further comprising a testing means for testing a physical condition of a user and for producing a value representative of said physical condition, said testing means being connected to said recording means such that said recording means records said value.

18. The combination syringe and apparatus of claim 15, further comprising a display recessed in said housing and connected to said recording means for displaying recorded data.

19. The combination syringe and apparatus of claim 15, wherein said input terminal and said output terminal are located on a cap of said plunger.

20. The combination syringe and apparatus of claim 19, wherein said input terminal is circular and positioned at the center of said cap and wherein said output terminal is ring-shaped and positioned concentrically to said input terminal.

21. The combination syringe and apparatus of claim 19, wherein said input contact is circular and positioned at the center of said field and wherein said output contact is ring-shaped and positioned concentrically to said input contact.

22. The combination syringe and apparatus of claim 19, wherein said field is bordered by a positioning means for aligning said cap on said field such that when said cap is placed within said positioning means, said input terminal contacts said input contact and said output terminal contacts said output contact.

23. The combination syringe and apparatus of claim 15, wherein said recording means comprise a digital memory unit.

24. The combination syringe and apparatus of claim 15, wherein said housing is sufficiently compact to enable said apparatus to be hand-held and carried by a user.

* * * * *